United States Patent [19] — Valjukas et al. — [11] 4,134,886 — [45] Jan. 16, 1979

United States Patent [19]

Valjukas et al.

[11] 4,134,886

[45] Jan. 16, 1979

[54] ANTI-HEMOCYTIC SERUM AND A METHOD FOR THE PREPARATION THEREOF

[76] Inventors: Juozas B. Valjukas, ulitsa Antakalne, 65, kv. 50; Marionas A. Babyanskas, ulitsa Melnikaites, 8, kv. 30; Pyatras A. Zayanchkauskas, ulitsa Cherno, 10, kv. 54, all of Vilnjus, U.S.S.R.

[21] Appl. No.: 868,516

[22] Filed: Jan. 11, 1978

[51] Int. Cl.$^2$ .................... A23J 1/06

[52] U.S. Cl. .................... 260/112 B; 424/101

[58] Field of Search .................... 260/112 B; 424/101

[56] References Cited

PUBLICATIONS

Olefir, Chemical Abstracts, vol. 79: 74,595 (1973).

*Primary Examiner*—Walter C. Danison

*Attorney, Agent, or Firm*—Robert E. Burns; Emmanuel J. Lobato; Bruce L. Adams

[57] ABSTRACT

The anti-hemocytic serum for suppressing the immunologic mechanism of insects which is inactivated blood plasma of immunized animals produced by immunization of animals with a hemocyte suspension separated from cells of the bodies of insects; the titre of hemocytoagglutinins of the anti-hemocytic serum is 1:256 to 1:2048. The method for the preparation of the anti-hemocytic serum resides in removing the alimentary tract from insects and the hemolymph, preserving the remaining cells of the bodies of insects and homogenizing them to form a hemocyte suspension, washing off the preservative from the suspension before immunization and immunizing animals 4 times with intervals of 5 days, injecting a 50% hemocyte suspension in an amount of 0.07 ml per 100 g of the weight of the animal, isolating the blood plasma of animals after immunization and inactivating it.

3 Claims, No Drawings

ANTI-HEMOCYTIC SERUM AND A METHOD FOR THE PREPARATION THEREOF

FIELD OF APPLICATION

The present invention relates to agriculture, and more particularly, to a new anti-hemocytic serum for suppressing the immunologic mechanism of insects and a method for the preparation thereof. The proposed new serum finds application in pest control of such insects cabbage white butterfly, bee moth, Colorado potato beetle and others.

There are known in the art various biological preparations for protecting plants from pests, for example such preparations as agritrol, bactan, biospore 2802, etc.

When these bacterial preparations are used pests soon acquire immunity to these preparations, and with prolonged application of these preparations they do not produce a positive effect.

BRIEF DESCRIPTION OF THE INVENTION

The proposed anti-hemocytic serum for suppressing the immunologic mechanism of insects is novel and has not been described in literature.

According to the invention, the proposed anti-hemocytic serum is inactivated plasma of the blood of immunized animals obtained by immunization of animals with a suspension of hemocytes isolated from the cells of bodies of animals; the titre of hemocytoagglutinins of the anti-hemocytic serum is 1:256 to 1:2048.

Unlike the known biological means of pest control the proposed serum suppresses the immunological reactivity of insect pests by retarding the synthesis of antibodies. The advantages of the proposed serum are destruction of insects by suppressing their immunity, the weakening of resistance of insects to bacteria, and the harmlessness of the serum to the environment.

The proposed serum can be used for controlling any species of insect pests, and for every species of insects a serum is used which has been prepared on the basis of cells of the body of an insect of the respective species.

According to the invention, the method for the preparation of the anti-hemocytic serum for suppressing the immunologic mechanism resides in removing the alimentary tract from the insects and the hemolymph, preserving the remaining cells of the bodies of insects and homogenizing them to form a suspension of hemocytes, washing off the preservative from the suspension before immunization, and immunizing animals four times with intervals of five days, injecting a 50% suspension of hemocytes in an amount of 0.07 ml per 100 g of the weight of an animal, removing the whole blood of animals after immunization, isolating the plasma of the blood and inactivating it.

The suspension of hemocytes is preferably preserved by adding a mixture consisting of the following components, in percent by weight:

| | |
|---|---|
| sodium citrate | 3.5 |
| glucose | 2.0 |
| chloramphenicol | 0.015 |
| distilled water | up to 100, |

then a solution consisting of 0.24 M of saccharose, 0.004 M of ethylene diamine tetra-acetic acid, 0.01 M of sodium phosphate per 1,000 ml of distilled water, pH of 7.0, and glycerin in a weight ratio of 1:2:1 respectively, is added to the resultant mixture which is kept at a temperature of −20° C. to ±2° C.

DETAILED DESCRIPTION OF THE INVENTION

The proposed method for the preparation of the anti-hemocytic serum is effected in the following manner.

Insects used as pests can be of different species such as *Galleria mellonella L, Pieris brassicae L* and others. The alimentary tract of insects is removed for preventing the action of enzymes and the hemolymph is also removed. The remaining cells of the bodies of insects are preserved in any suitable preservative and homogenized to form a suspension of hemocytes. The following composition is used as a preservative ensuring the prevention of reactions of agglutination, melinization and oxidation, in percent by weight:

| | |
|---|---|
| sodium citrate | 3.5 |
| glucose | 2.0 |
| chloramphenicol | 0.015 |
| distilled water | up to 100. |

To keep the hemocyte suspension at a temperature of −20° C. to ±2° C. and to preserve the integrity of cells a solution consisting of 0.24 M of saccharose, 0.004 M of ethylene diamine tetra-acetic acid, 0.01 M of sodium phosphate per 1,000 ml of distilled water, pH of 7.0, and glycerin in a ratio of 1:2:1 respectively, is added to the resultant solution.

Immunization of animals is carried out with the produced hemocyte suspension. For this purpose the hemocyte suspension is washed beforehand with a physiological solution to remove the preservative.

Immunization of animals is then carried out four times with intervals of 5 days by means of injecting a 50% hemocyte suspension in an amount of 0.07 ml per 100 g of the weight of the animal.

After immunization is over the whole blood of animals is removed, the plasma of the blood is separated and inactivated by keeping it at 56° C. for 30 minutes.

The resultant anti-hemocytic serum has a titre of hemocytoagglutinins of 1:256 to 1:2048.

The proposed anti-hemocytic serum was tested on different species of insects. It was applied by spraying. The test results showed a high activity of the proposed serum. The death rate of insects of the first generation was from 35 to 75%, of the second generation from 85 to 100%, depending on the dose of the serum applied to insects. The proposed serum can also be used in combination with entomopathogenic bacteria.

For a better understanding of the present invention the following examples illustrating the method for the preparation of the anti-hemocytic serum and the methods for testing its activity are presented below.

Example 1. Caterpillars of *Galleria mellonella L* in an amount of 2,000 in the period of their development (nistars V and VI) are disinfected with ethyl alcohol and left for 5 to 6 hours for cleaning the alimentary tract. The live caterpillars are placed in a preservative consisting of the following components, in grams; sodium citrate 3.5; glucose 2.0; cloramphenicol 0.015; distilled water up to 100. The preservative is taken in an amount of 1 ml per 10 caterpillars. Then one segment is removed from the front portion and one segment from the rear portion of the bodies of caterpillars. The alimentary tract is removed to prevent the action of enzymes. The remaining bodies of caterpillars are ground and placed together with said preservative in a magnetic mixer for 7 to 10 minutes for the complete separation of hemolymph. The resultant homogenate is filtered and centrifuged 6 to 7 times for 15 minutes at 1,000 r.p.m. The centrifugate is left for 30 minutes at room temperature and the upper fat-like layer is removed with a cottonwool wad. The plasma of the hemolymph is poured off and a solution consisting of 0.24 M of saccharose, 0.004 M of ethylene diamine tetraacetic acid, 0.01 M of sodium phosphate per 1,000 ml of distilled water, pH of 7.0, and glycerin in a weight ratio of 1:2:1 respectively, is poured onto the cells. The resultant hemocyte suspension is kept until immunization of animals at a temperature of −20° C.±2° C. Prior to immunization the hemocyte suspension is washed with a physiological solution to remove the preservative. Immunization of 12 white rats with a weight of 300 g each is carried out 4 times with intervals of 5 days. Each time 0.2 ml of a 50% hemocyte solution is injected. The first immunization is done subcutaneously injecting 0.2 ml of a 50% hemocyte solution into every rat. The subsequent immunizations are done intramuscularly and each time 0.2 ml of a 50% hemocyte solution is injected in mixture with 16,666 units of penicillin to prevent possible infection.

Blood samples are taken from rats prior to the first immunization to determine the presence of natural antibodies in them against hemocytes of caterpillars. Seven days after the last immunization rats are dehematized. The separated blood is placed in glass cylinders and left at room temperature for 24 hours. The settled plasma of the blood is poured off and inactivated at 56° C. for 30 minutes. The anti-hemocytic serum is produced in an amount of 15 ml. The titre of hemocytoagglutinins is 1:2048.

The anti-hemocytic serum was tested on caterpillars of *Galleria mellonella L* in the period of their development (II-IV and V-VI nistars). Caterpillars were sprayed with the anti-hemocytic serum in doses of 0.25 to 2.5 microliters for each caterpillar. The effect of the anti-hemocytic serum on the immunologic reactivity of the insects organisms was checked every 6 hours. At the same time the anti-hemocytic serum was tested in combination with entomopathogenic bacteria *Bac.thuringiensis cereus var.galleriae.* The anti-hemocytic serum was used in doses of from 0.25 to 2.5 microliters for each caterpillar. *Bac.thuringiensis cereus var. galleriae* was used as a 0.1% water suspension in treating caterpillars of the first generation and as a 0.01% water suspension in treating caterpillars of the second generation.

A control experiment (without treating caterpillars) and treatment of caterpillars with heterogeneous proteins and entomopathogenic bacteria *Bac.thuringiensis cereus var. galleriae* were carried out to compare the activity.

The effect on the viability of caterpillars was checked every 6 hours from the beginning of experiments.

The maximum intensity of destruction of caterpillars *Galleria mellonella L* was achieved in the period from 12 to 18 hours from the beginning of the experiment.

The test results are given in Tables 1 and 2.

Table 1

Suppression of Immunologic Mechanism of Insects with Anti-Hemocytic Serum and the Effect of *Bac. thuringiensis cereus var.galleriae* on Viability of Caterpillars *Galleria mellonella* (First Generation)

| | Effectiveness of Destruction of caterpillars, in % | | | | | | | |
|---|---|---|---|---|---|---|---|---|
| | Destruction of caterpillars less than 24 hours | | Destruction of caterpillars after 24 hours | | Destruction of caterpillars in less than 24 hours | | Destruction of caterpillars after 24 hours | |
| Types of experiments | Nistar II | Nistar IV | Nistar II | Nistar IV | Nistar V | Nistar VI | Nistar V | Nistar VI |
| 1. Check experiment (without treating caterpillars) | 0 | 0 | 0 | 0 | 0 | 0 | 0 | 0 |
| 2. Treatment with heterogeneous proteins | 0 | 0 | 1 | 1 | 0 | 0 | 1 | 1 |
| 3. Treatment with entomopathogenic bacteria *Bac. thuringiensis cereus var. galleriae* | 0 | 0 | 16 | 16 | 0 | 0 | 14 | 14 |
| 4. Treatment with anti-hemocytic serum | 32 | 32 | 32 | 32 | 32 | 32 | 32 | 32 |
| 5. Treatment with anti-hemocytic serum in combination with *Bac. thuringiensis cereus var.galleriae* | 75 | 75 | 75 | 75 | 75 | 75 | 75 | 75 |

Table 2

Suppression of Immunologic Mechanism of Insects with Anti-Hemocytic Serum and the Effect of *Bac.thuringiensis cereus var. galleriae* on Viability of Caterpillars *Galleria mellonella* (Second Generation)

| | Effectiveness of Destruction of Caterpillars,in % | | | | | | | |
|---|---|---|---|---|---|---|---|---|
| | Destruction of caterpillars in less than 24 hours | | Destruction of caterpillars after 24 hours | | Destruction of caterpillars in less than 24 hours | | Destruction of caterpillars after 24 hours | |
| Types of experiments | Nistar II | Nistar IV | Nistar II | Nistar IV | Nistar V | Nistar VI | Nistar V | Nistar VI |
| 1. Check experiment (without treating caterpillars) | 0 | 0 | 0 | 0 | 0 | 0 | 0 | 0 |
| 2. Treatment with heterogeneous proteins | 0 | 0 | 0 | 0 | 0 | 0 | 0 | 0 |
| 3. Treatment with entomopathogenic bacteria *Bac.thuringiensis cereus var.galleriae* | 0 | 0 | 8 | 8 | 0 | 0 | 2 | 3 |
| 4. Treatment with hemo- | | | | | | | | |

Table 2-continued

| Types of experiments | Suppression of Immunologic Mechanism of Insects with Anti-Hemocytic Serum and the Effect of *Bac.thuringiensis cereus var. galleriae* on Viability of Caterpillars *Galleria mellonella* (Second Generation) Effectiveness of Destruction of Caterpillars,in % | | | | | | | |
|---|---|---|---|---|---|---|---|---|
| | Destruction of caterpillars in less than 24 hours | | Destruction of caterpillars after 24 hours | | Destruction of caterpillars in less than 24 hours | | Destruction of caterpillars after 24 hours | |
| | Nistar II | Nistar IV | Nistar II | Nistar IV | Nistar V | Nistar VI | Nistar V | Nistar VI |
| cytic serum | 85 | 85 | 85 | 85 | 85 | 85 | 85 | 85 |
| 5. Treatment with anti-hemocytic serum and *Bac.thuringiensis cereus var.galleriae* | 100 | 100 | 100 | 100 | 100 | 100 | 100 | 100 |

Comparing the data given in the tables it can be seen that in treating caterpillars *G.mellonella L* with the anti-hemocytic serum their death rate in the second generation reaches 100% whereas due to the use of entomopathogenic bacteria in the second generation the efficiency of destruction of caterpillars diminishes since they acquire immunity against these bacteria.

Example 2. Insects used are caterpillars of cabbage white butterfly *Pieris brassicae L.* The process of preparation of the anti-hemocytic serum is identical with that of Example 1.

The tests of the anti-hemocytic serum produced are identical with those of Example 1.

Caterpillars of *Pieris brassicae L* were treated with the anti-hemocytic serum in doses of 0.25 microliters to 4.5 microliters as well as with the anti-hemocytic serum in combination with entomopathogenic bacteria *Bac.-thuringiensis cereus var. galleriae* which were used as a 0.1% water suspension in doses of 0.016 ml for every caterpillar. The test results are given in Tables 3 and 4.

Table 3

| Type of preparation | Dose of treatment for every caterpillar, in micro-liters | Effectiveness of destruction of caterpillars, in % |
|---|---|---|
| 1. Anti-hemocytic serum | 0.25 | 30 |
| " | 0.5 | 32 |
| " | 0.75 | 40 |
| " | 1.0 | 40 |
| " | 1.25 | 50 |
| " | 1.50 | 58 |
| " | 1.75 | 70 |
| " | 2.5 | 98 |
| " | 4.5 | 100 |
| 2. Control experiment (distilled water) | 0.25 | 0 |

Table 3-continued

| Type of preparation | Dose of treatment for every caterpillar, in micro-liters | Effectiveness of destruction of caterpillars, in % |
|---|---|---|
| 3. " | 4.5 | 0 |

Table 4

| No. | Type of preparation | Dose of treatment for every caterpillar | Effectiveness of destruction of caterpillars, in % |
|---|---|---|---|
| 1. | Anti-hemocytic serum in combination with entomopathogenic bacteria *Bac. thuringiensis cereus var. galleriae* | 0.25 µl +0.016 ml of a 0.1% water suspension of bacteria | 50 |
| | | 0.5µl+0.016 ml of a 0.1% water suspension of bacteria | 67 |
| | | 1.0 µl +0.016 ml of a 0.1% water suspension of bacteria | 83 |
| | | 2.5 µl +0.016 ml of a 0.1% water suspension of bacteria | 100 |
| | | 4.5µl+0.016 ml of a 0.1% water suspension of bacteria | 100 |
| 2. | Control experiment (without treatment) | — | 0 |
| 3. | Control experiment (distilled water) | 2.5 µl | 0 |

What is claimed is:

1. Anti-hemocytic serum for suppressing the immunologic mechanism of insects which is inactivated plasma of the blood of immunized animals produced by immunization of animals with a hemocyte suspension separated from cells of the bodies of insects; the titre of hemocytoagglutinins of the anti-hemocytic serum is 1:256 to 1:2048.

2. A method for the preparation of anti-hemocytic serum as claimed in claim 1, residing in removing the alimentary tract from the insects and the hemolymph, preserving the remaining cells of the bodies of insects and homogenizing them to form a hemocyte suspension, washing off the preservative from the suspension prior to immunization, and immunizing animals 4 times with intervals of 5 days, injecting a 50% hemocyte suspension in an amount of 0.07 ml per 100 g of the weight of the animal, isolating the blood plasma of animals after immunization and inactivating it.

3. A method as claimed in claim 2, whereby the hemocyte suspension is preserved by adding a mixture consisting of the following components, in percent by weight:

| | |
|---|---|
| sodium citrate | 3.5 |
| glucose | 2.0 |
| chloramphenicol | 0.015 |
| distilled water | up to 100, |

then a solution consisting of 0.24 M of saccharose, 0.004 M of ethylene diamine tetra-acetic acid, 0.01 M of sodium phosphate for 1,000 ml of distilled water, pH of 7.0, and glycerin in a ratio of 1:2:1 respectively, is added to the resultant mixture, and the resultant mixture is kept at −20° C. ± 2° C.

* * * * *